United States Patent
Colvin et al.

(10) Patent No.: US 11,173,053 B2
(45) Date of Patent: Nov. 16, 2021

(54) COMPOSITE PROSTHETIC FOOT STRUCTURE

(71) Applicant: WillowWood Global LLC, Mount Sterling, OH (US)

(72) Inventors: James M. Colvin, Hilliard, OH (US); Matthew M. Wernke, Tampa, FL (US); Stephen A. Byers, Dublin, OH (US); Evandro M. Ficanha, Grove City, OH (US)

(73) Assignee: WILLOWWOOD GLOBAL LLC, Mount Sterling, OH (US)

( * ) Notice: Subject to any disclaimer, the term of this patent is extended or adjusted under 35 U.S.C. 154(b) by 0 days.

(21) Appl. No.: 16/808,796

(22) Filed: Mar. 4, 2020

(65) Prior Publication Data

US 2021/0275327 A1  Sep. 9, 2021

(51) Int. Cl.
*A61F 2/66* (2006.01)

(52) U.S. Cl.
CPC ........ *A61F 2/66* (2013.01); *A61F 2002/6621* (2013.01); *A61F 2002/6642* (2013.01); *A61F 2002/6657* (2013.01)

(58) Field of Classification Search
CPC ...... A61F 2/60; A61F 2/66; A61F 2002/6657; A61F 2002/6642; A61F 2002/6621
See application file for complete search history.

(56) References Cited

U.S. PATENT DOCUMENTS

| | | | |
|---|---|---|---|
| 4,822,363 A * | 4/1989 | Phillips | A61F 2/60 623/27 |
| 5,314,282 A | 5/1994 | Murphy et al. | |
| 5,361,483 A | 11/1994 | Rainville et al. | |
| 7,351,022 B2 | 4/2008 | Denslow | |
| 7,419,509 B2 * | 9/2008 | Christensen | A61F 2/66 623/52 |
| 8,900,326 B2 | 12/2014 | Doddroe et al. | |
| 2005/0125985 A1 | 6/2005 | Adams et al. | |
| 2010/0332002 A1* | 12/2010 | Nelson | A61F 2/6607 623/55 |
| 2016/0061245 A1 | 3/2016 | Toyozumi et al. | |
| 2018/0296370 A1* | 10/2018 | Jonsson | A61F 2/66 |
| 2020/0375765 A1* | 12/2020 | Friesen | A61F 2/66 |

* cited by examiner

*Primary Examiner* — Bruce E Snow
(74) *Attorney, Agent, or Firm* — Thompson Hine LLP

(57) ABSTRACT

A prosthetic foot structure includes a plate assembly having a toe portion and a heel portion. The plate assembly includes a first plate adjoining a second plate along a seam at which the first plate is bonded to the second plate. The seam has an end between the first and second plates, and the first plate is spaced from the second plate across a gap that reaches away from the end of the seam. An attachment structure attaches the first plate to second plate. The attachment structure has a composite composition including a resin material containing reinforcing fibers. The reinforcing fibers reach through the first plate, across the gap, and through the second plate.

39 Claims, 6 Drawing Sheets

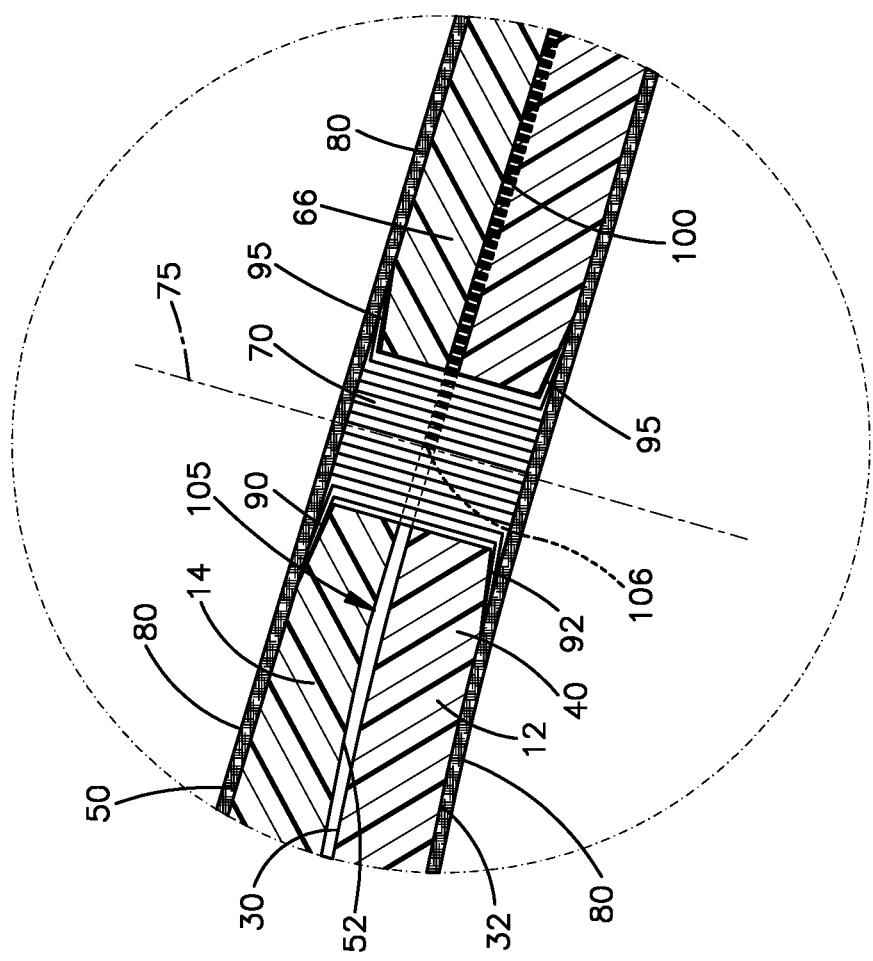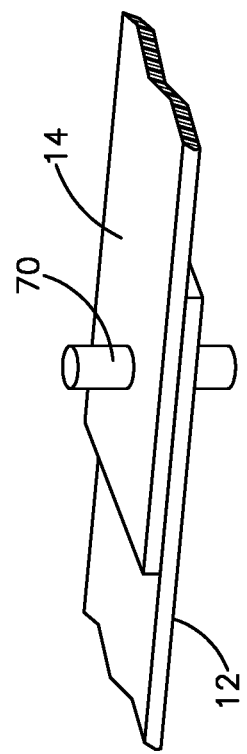

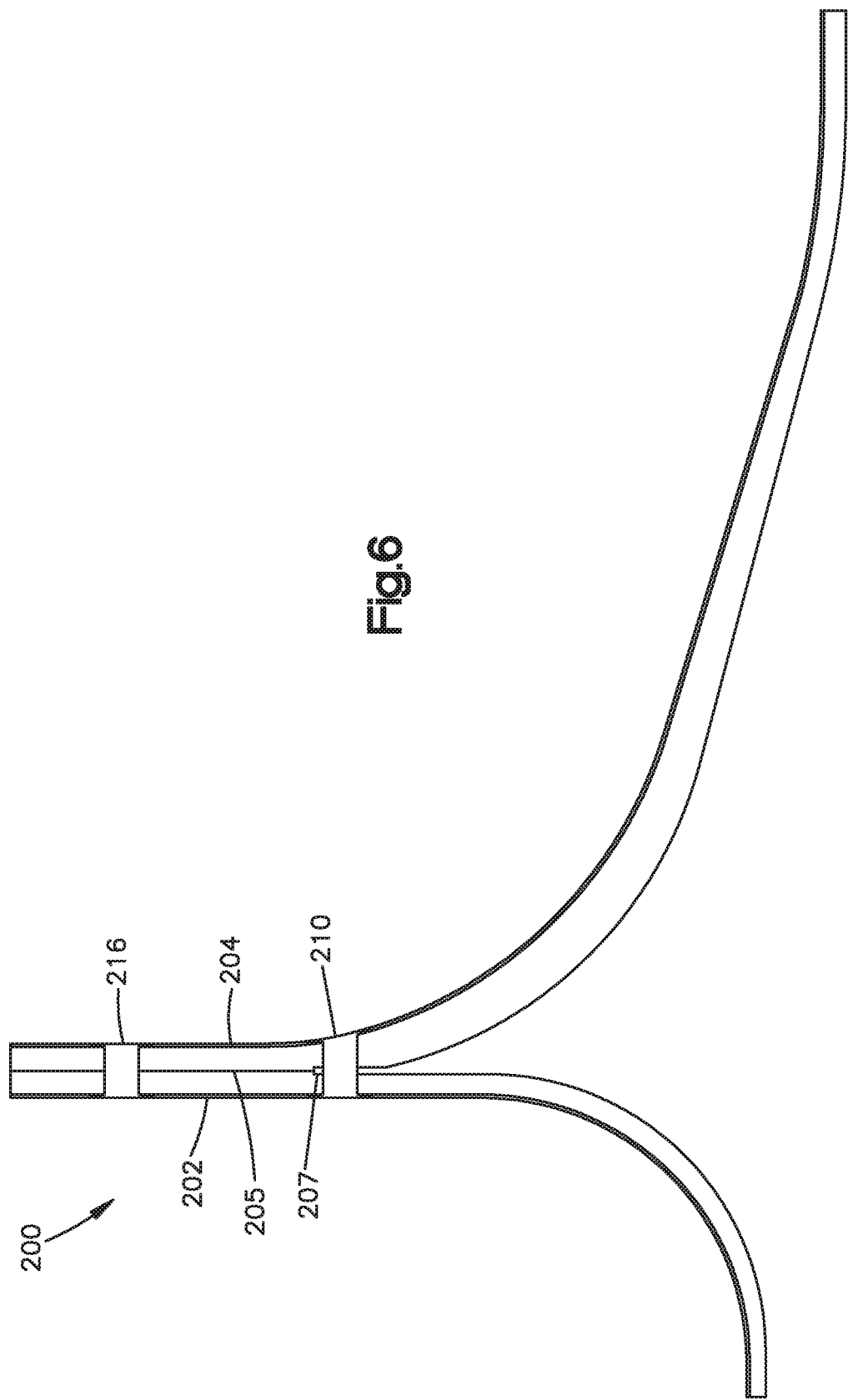

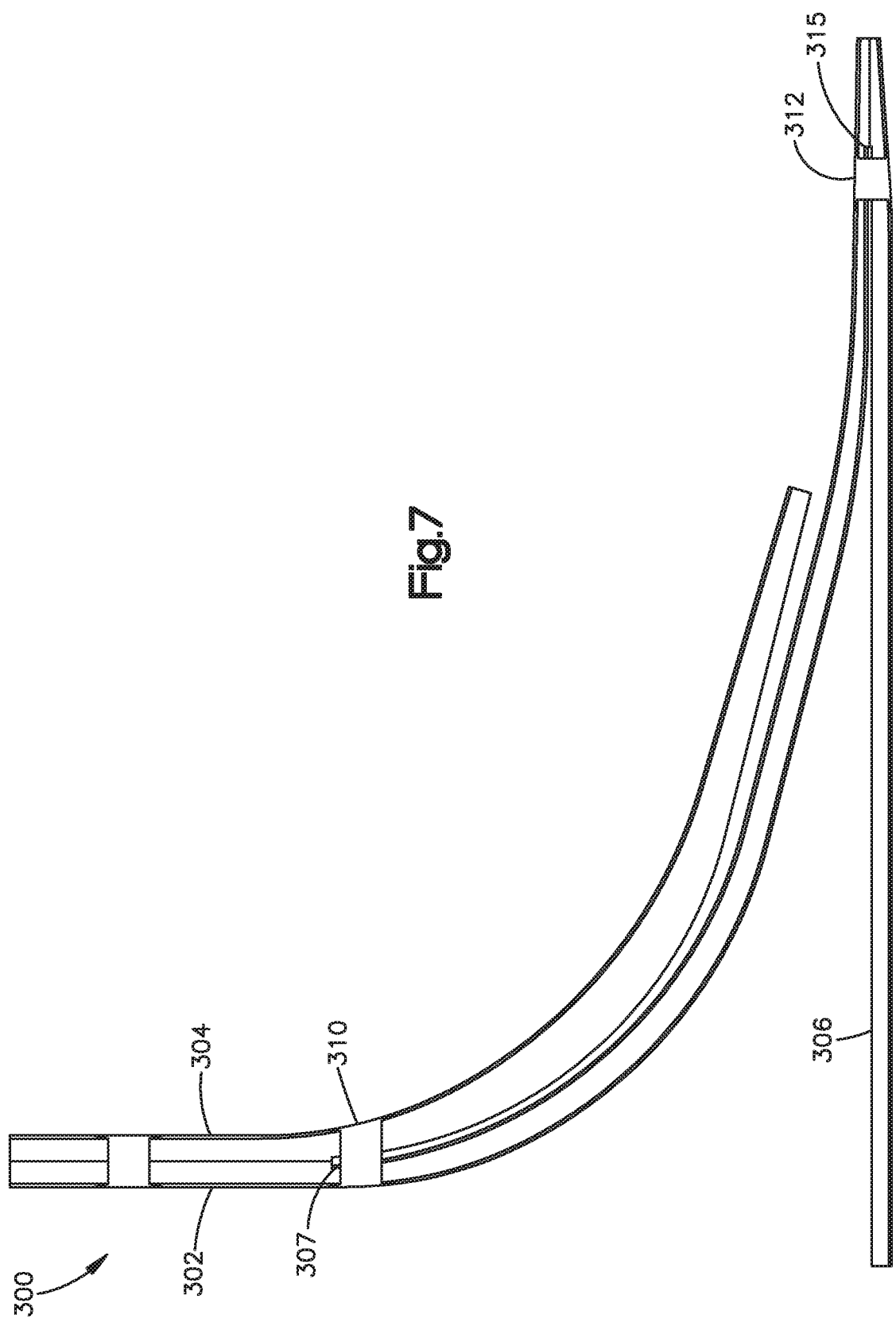

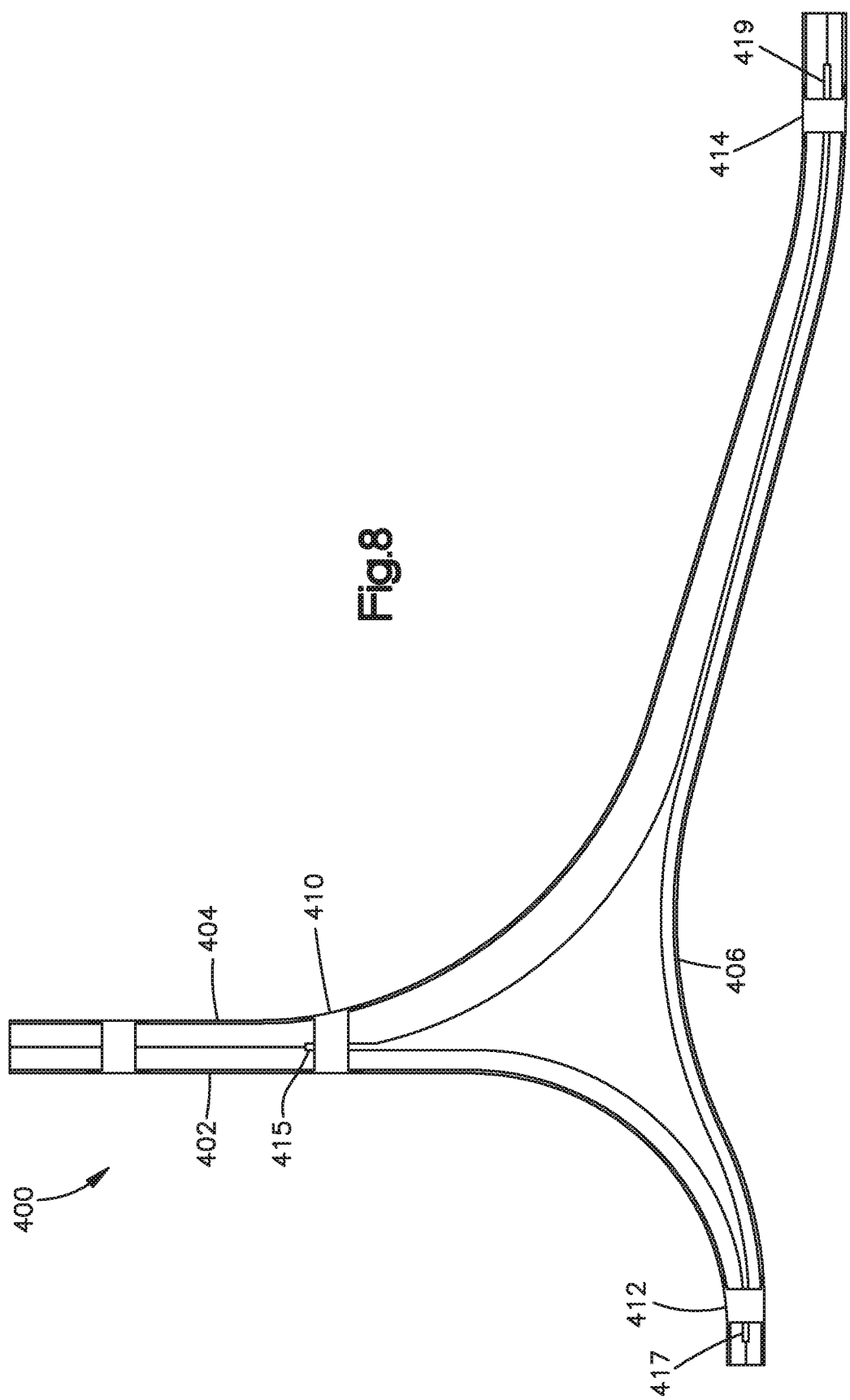

COMPOSITE PROSTHETIC FOOT STRUCTURE

STATEMENT OF FEDERALLY FUNDED RESEARCH

This invention was made with government support under 2R42HD093476-02A1 awarded by the National Institutes of Health; Eunice Kennedy Shriver National Institute of Child Health& Human Development. The government has certain rights in the invention.

TECHNICAL FIELD

This technology includes weight-bearing structural components of a prosthetic foot.

BACKGROUND

A prosthetic foot may have structural components including a foot plate. The foot plate may have a toe portion, a heel portion, and an intermediate portion with an arched configuration that flexes under the weight of the user as needed throughout the gait cycle. The structural components may also include a shank plate in addition to the foot plate. The shank plate has a vertical upper portion for connection with another prosthetic device such as, for example, a prosthetic knee. The shank plate may further have a lower portion with a curvature reaching forward from the upper portion. The lower portion of the shank plate also flexes under the weight of the user, and is fastened to the foot plate to transmit the weight load forces to the foot plate.

SUMMARY

A prosthetic foot structure includes a plate assembly having a toe portion and a heel portion. The plate assembly includes a first plate adjoining a second plate along a seam at which the first plate is bonded to the second plate. The seam has an end between the first and second plates, and the first plate is spaced from the second plate across a gap that reaches away from the end of the seam.

An attachment structure attaches the first plate to the second plate. The attachment structure has a composite composition including a resin material containing reinforcing fibers. The reinforcing fibers reach through the first plate, across the gap, and through the second plate.

In some embodiments, the first plate is a foot plate having a toe portion and a heel portion. The second plate is a shank plate having an upper portion and a lower portion. The upper portion of the shank plate projects vertically upward. The lower portion of the shank plate overlies the foot plate along a seam at which the shank plate is bonded to the foot plate.

An attachment structure attaches the shank plate to the foot plate. The attachment structure has a composite composition including a resin material containing reinforcing fibers. The reinforcing fibers in the attachment structure reach through the foot plate and through the shank plate in uni-directional alignment. Additionally, the fibers in a top portion the attachment structure diverge above a top surface of the shank plate, and the fibers in a bottom portion of the attachment structure diverge beneath a bottom surface of the foot plate.

A layer of fiber-reinforced resin material may overlie the top surface of the shank plate and the top portion of the attachment structure. Another layer of fiber-reinforced resin material may underlie the bottom surface of the foot plate and the bottom portion of the attachment structure.

BRIEF DESCRIPTION OF THE DRAWINGS

FIG. 3 is an enlarged view showing parts of the prosthetic foot structure in a partially assembled condition.

FIG. 4 is an enlarged view of parts shown in FIG. 1.

FIG. 5 is a view similar to FIG. 4, showing parts of an alternative embodiment of the prosthetic foot structure.

FIG. 6 is a view similar to FIG. 4, showing parts of an alternative embodiment of the prosthetic foot structure.

FIG. 7 is a view similar to FIG. 4, showing parts of an alternative embodiment of the prosthetic foot structure.

FIG. 8 also is a view similar to FIG. 4, showing parts of an another alternative embodiment of the prosthetic foot structure.

DETAILED DESCRIPTION

Figure 1:
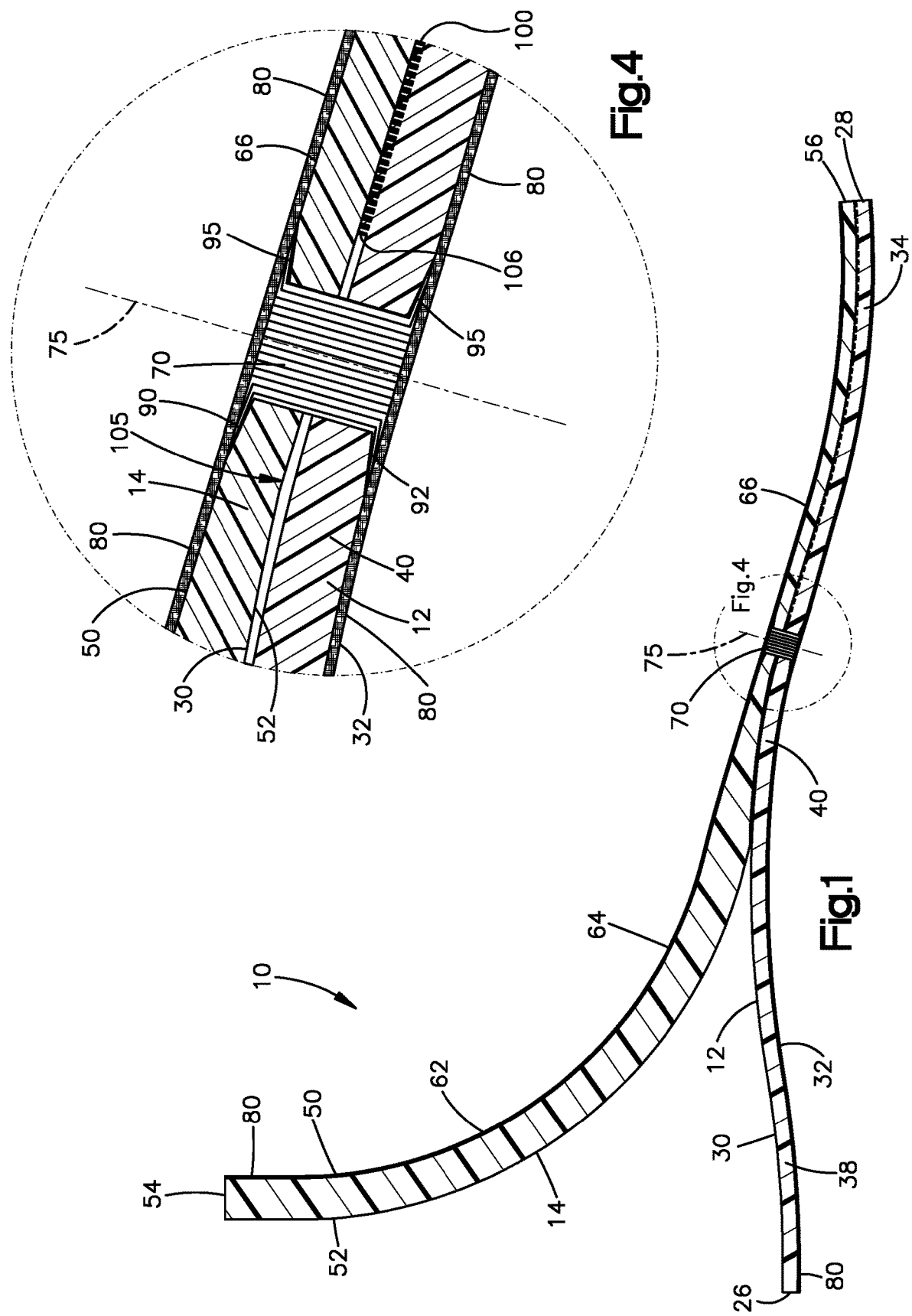
FIG. 1 is a sectional side view of a prosthetic foot structure.

The structures illustrated in the drawings includes parts that are examples of the structural elements recited in the claims. The illustrated structures thus include examples of how a person of ordinary skill in the art can make and use the claimed invention. They are described here to meet the enablement and best mode requirements of the patent statute without imposing limitations that are not recited in the claims. One or more elements of one embodiment may be used in combination with, or as a substitute for, one or more elements of another as needed for any particular implementation of the claimed invention.

As shown in FIG. 1, a prosthetic foot structure 10 includes a plate assembly comprising a foot plate 12 and a shank plate 14. The foot structure 10 may be combined with other parts (not shown) of a complete prosthetic foot. Such other parts may include, for example, a cosmetic foot shell. The foot plate 12 and the shank plate 14 both have strength and stiffness as needed to support the user's weight, and also have flexibility as needed to serve as springs for comfort and assistance in the heel strike and toe-off stages of the gait cycle.

Figure 2:
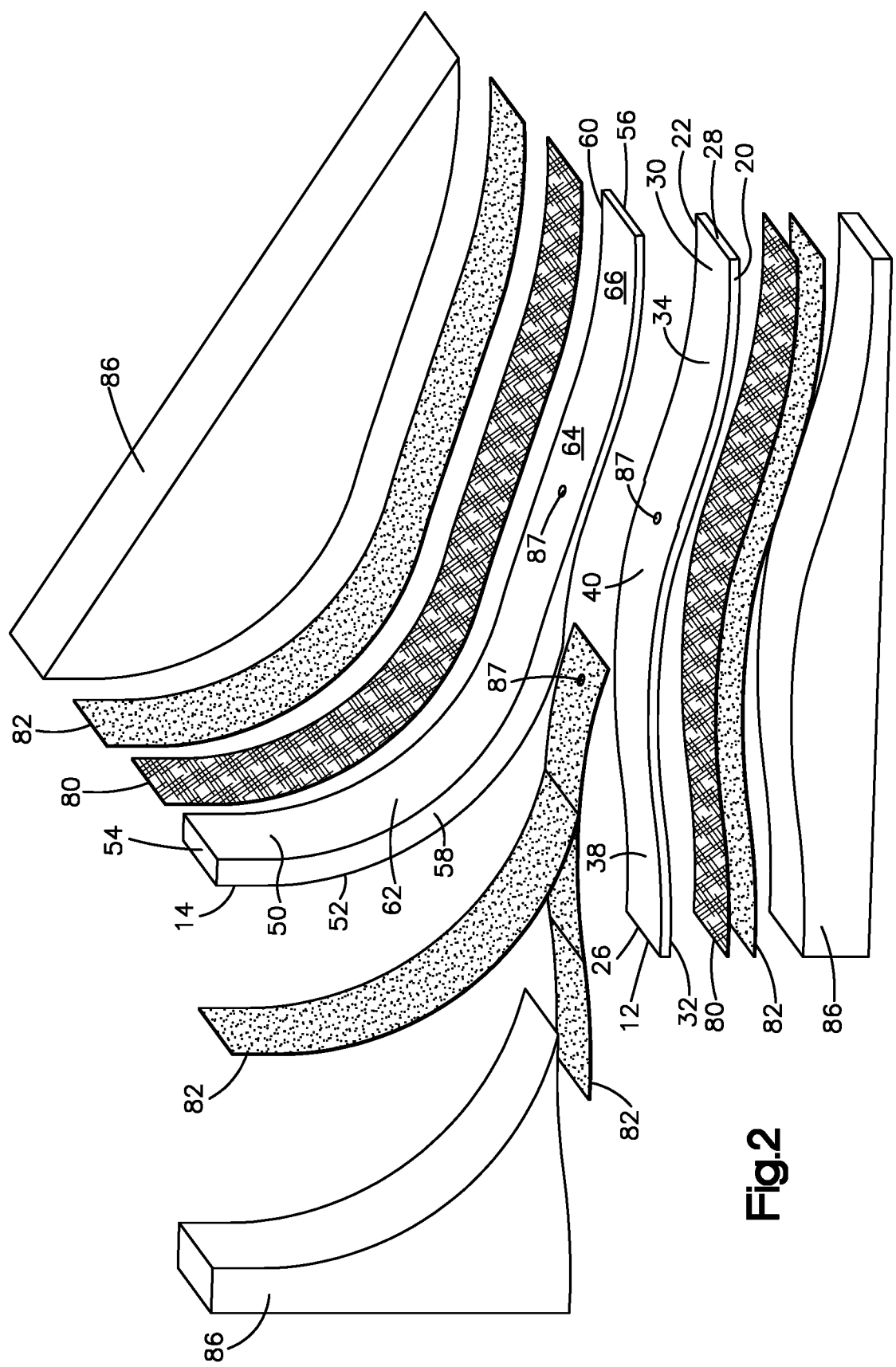
FIG. 2 is an exploded view of parts of the prosthetic foot structure of FIG. 1.

As shown in FIGS. 1 and 2, the foot plate 12 has a narrow elongated shape with opposite side edges 20 and 22 reaching longitudinally between opposite end edges 26 and 28. Top and bottom side surfaces 30 and 32 define the length of the foot plate 12 between the opposite end edges 26 and 28, as well as the width of the foot plate 12 between the opposite side edges 20 and 22. The top and bottom side surfaces 30 and 32 have contours defining generally distinct length portions of the foot plate 12, including a toe portion 34, a heel portion 38, and an arched intermediate portion 40.

The shank plate 14 also has an elongated shape with top and bottom side surfaces 50 and 52 defining its length and width between opposite end edges 54 and 56 and opposite side edges 58 and 60. The top and bottom side surfaces 50 and 52 have contours defining an upper portion 62, an intermediate portion 64, and a lower portion 66 of the shank plate 14.

As further shown in FIG. 1, an attachment structure 70 attaches the shank plate 14 to the foot plate 12. In the attached condition of FIG. 1, the upper portion 62 of the shank plate 14 is oriented vertically for connection with another component of a prosthetic leg, such as a socket or a knee joint. The lower portion 66 of the shank plate 14 overlies the intermediate and toe portions 40 and 34 of the foot plate 14. The curvature of the intermediate portion 64 of the shank plate 14 provides a flexible transition between the upper portion 62 and the lower portion 66.

Both the foot plate 12 and the shank plate 14 are formed of a composite material including reinforcing fibers embedded in a resin binder. The fibers are primarily aligned uni-directionally lengthwise of each plate 12 and 14.

The attachment structure 70 also is formed of a composite material including reinforcing fibers embedded in a resin binder. However, the fibers in the attachment structure 70 are primarily aligned uni-directionally along a transverse axis 75 normal to the lengthwise directions of the plates 12 and 14. The fibers in the attachment structure 70 thus reach through the plates 12 and 14 primarily in a common direction through the thickness of the plates 12 and 14 instead of along the lengths of the plates 12 and 14.

As shown in FIG. 2, additional parts of the foot structure 10 include layers 80 of composite weave material. One layer 80 of composite weave material is provided to overlie the shank plate 14. Another layer of composite weave material 80 is provided to underlie the foot plate 12. Layers 82 of peel ply film are placed between the plates 12 and 14 and three surrounding mold parts 86.

As further shown in FIG. 2, the foot plate 12, the shank plate 14, and an intervening layer 82 of peel ply film are provided with apertures 87. As shown in FIG. 3, the attachment structure 70 is provided as sheet of the composite material that is rolled into the shape of a cylinder. When the components of FIG. 2 are being placed together in the mold, the apertures 87 are aligned on the transverse axis 75, and the cylindrical attachment structure 70 is inserted thought the aligned apertures 87.

The attachment structure 70 is deflected into the configuration shown in FIG. 4. This provides the attachment structure 70 with flattened top and bottom end portions 90 and 92. As indicated schematically in FIG. 4, the reinforcing fibers in the end portions 90 and 92 diverge radially outward over the top surface 50 of the shank plate 14 and the bottom surface 32 of the foot plate 12. The top and bottom surfaces 50 and 32 of the plates 14 and 12 may be provided with recesses 95 to receive the deflected end portions 90 and 92 of the attachment structure 70, as shown in FIG. 4, and thereby to avoid a surface bulge at each of those locations. Alternatively, the deflected end portions 90 and 92 may be pressed onto the top and bottom surfaces 50 and 32 without the recesses 95. The overlying and underlying layers 80 of composite weave material also help to provide smooth surfaces over the deflected end portions 90 and 92 of the attachment structure 70.

The resin materials in the plates 12 and 14, the composite weave layers 80, and the attachment structure 70 are next cured together against the mold. A single curing process bonds all of the adjoining composite materials together. This forms a seam 100 along which the shank plate 14 is bonded to the foot plate 12. The seam 100 reaches rearward from the forward ends of the plates 12 and 14, until the forward end of a layer 82 of peel ply film blocks the formation of a bond where it reaches between the shank plate 14 and the foot plate 12. That layer 82 of peel ply film is optionally removed to expose a gap 105 (FIG. 4) across which the bottom surface 52 of the shank plate 14 is spaced apart from the top surface 30 of the foot plate 12. The gap 105 enables the shank plate 14 and the foot plate 12 to deflect independently of one another at that location. The optional removal of the layer 82 of peel ply film does not affect the mechanical characteristics of the prosthetic foot structure 10 and has the sole purpose to improve the cosmetic appearance of the final part.

As the plates 12 and 14 deflect across the gap 105, stresses can concentrate at the rear end 106 of the seam 100 where the plates 12 and 14 cannot flex independently. However, the attachment structure 70 is located so as to bear the load of these stresses to prevent separation of the plates 12 and 14 at the seam 100. Specifically, if the seam 100 were extended to reach rearward past the attachment structure 70, a rearwardly extending section of the seam 100 could rupture as the plates 12 and 14 deflect away from one another. For this reason the attachment structure 70 is located at least partially to the rear of the seam 100 so that the seam 100 does not reach rearward past the attachment structure 70. In the example shown in FIGS. 1 and 2, the attachment structure 70 is located entirely to the rear of the seam 100. In the example shown in FIG. 5, the attachment structure is located partially within the gap 105 beside the rear end 106 of the seam 100. In each of these examples, the fibers in the attachment structure 70 are primarily aligned uni-directionally with the transverse axis 75 along their lengths reaching through the foot plate 12, the gap 105, and the shank plate 14.

In the alternative embodiment of FIG. 6, a plate assembly in a prosthetic foot structure 200 includes first and second plates 202 and 204. These plates 202 and 204 have composite compositions substantially the same as the composite compositions of the plates 12 and 14 described above. The plates 202 and 204 are joined along a seam 205 that terminates at a gap 207. The foot structure 200 further includes an attachment structure 210 having substantially the same composition and structural configuration as the attachment structure 70 described above. The attachment structure 210 thus reaches through the plates 202 and 204 and across the gap 207 to prevent separation of the plates 202 and 204 at the seam 207. One or more additional attachment structures 216 may also be provided.

Additional alternative embodiments are shown in FIGS. 7 and 8. In the embodiment of FIG. 7, the foot structure 300 includes three composite plates 302, 304, and 306 attached together by two composite attachment structures 310 and 312. One of these attachment structures 310 reaches through the plates 302, 304 and a gap 307 between the plates 302, 304. The other attachment structure reaches through the plates 302, 306 and a gap 315 between those plates 302, 306. In the embodiment of FIG. 8, the foot structure 400 similarly includes three composite plates 402, 404, and 406 with three composite attachment structures 410, 412 and 414 at respective gaps 415, 417, and 419. One or more additional attachment structures also may be provided in the embodiments of FIGS. 7 and 8, as shown.

This written description sets for the best mode of carrying out the invention, and describes the invention so as to enable a person of ordinary skill in the art to make and use the invention, by presenting examples of the elements recited in the claims. The detailed descriptions of those elements do not impose limitations that are not recited in the claims, either literally or under the doctrine of equivalents.

The invention claimed is:

1. A prosthetic foot structure comprising:
   a plate assembly having a toe portion and a heel portion, including a first plate adjoining a second plate along a seam at which the first plate is bonded to the second plate, wherein the seam has an end between the first and second plates, and the first plate is spaced from the second plate across a gap that reaches away from the end of the seam; and an attachment structure attaching the first plate to second plate, wherein the attachment structure has a composite composition including a resin material containing reinforcing fibers, and the reinforcing fibers reach through the first plate, across the gap, and through the second plate.

2. A prosthetic foot structure as defined in claim 1, wherein the first plate is a foot plate reaching rearward from the toe portion of the plate assembly.

3. A prosthetic foot structure as defined in claim 2, wherein the second plate is a shank plate having a vertical upper portion and a lower portion that overlies the foot plate along the seam.

4. A prosthetic foot structure as defined in claim 1, wherein the first plate is a shank plate having a vertical upper portion, and the second plate is a heel plate reaching forward from the heel end of the plate assembly.

5. A prosthetic foot structure as defined in claim 4, wherein the heel plate has vertical upper portion adjoining the shank plate along the seam.

6. A prosthetic foot structure as defined in claim 1, wherein the first plate is a foot plate reaching rearward from the toe portion of the plate assembly, and the second plate is a heel plate reaching forward from the heel end of the plate assembly.

7. A prosthetic foot structure as defined in claim 6, wherein the heel plate has a lower portion that overlies the foot plate along the seam.

8. A prosthetic foot structure as defined in claim 1, wherein the first and second plates are shank plates having vertical upper portions that adjoin along the seam.

9. A prosthetic foot structure as defined in claim 1, wherein the first and second plates have side surfaces facing in opposite directions away from one another, and the reinforcing fibers are uni-directionally aligned fully between the side surfaces.

10. A prosthetic foot structure as defined in claim 9, wherein the attachment structure has an end portion in which the reinforcing fibers diverge across the side surface of the first plate.

11. A prosthetic foot structure as defined in claim 10, further comprising a layer of fiber-reinforced resin material overlying the side surface of the first plate and the end portion of the attachment structure.

12. A prosthetic foot structure as defined in claim 10, wherein the attachment structure has an opposite end portion in which the reinforcing fibers diverge across the side surface of the second plate.

13. A prosthetic foot structure as defined in claim 12, further comprising a layer of fiber-reinforced resin material overlying the side surface of the foot plate and the opposite end portion of the attachment structure.

14. A prosthetic foot structure as defined in claim 1, wherein the first plate has a composite composition including a resin material containing reinforcing fibers.

15. A prosthetic foot as defined in claim 14, wherein the reinforcing fibers in the first plate are primarily aligned uni-directionally.

16. A prosthetic foot structure as defined in claim 14, wherein the first plate is elongated and the reinforcing fibers in the first plate are primarily aligned uni-directionally lengthwise of the first plate.

17. A prosthetic foot structure as defined in claim 16, wherein the second plate has a composite composition including a resin material containing reinforcing fibers, the second plate is elongated, and the reinforcing fibers in the second plate are primarily aligned uni-directionally lengthwise of the second plate.

18. A prosthetic foot structure comprising:
a foot plate having a toe portion and a heel portion;
a shank plate having a vertical upper portion and a lower portion that overlies the foot plate along a seam at which the shank plate is bonded to the foot plate, wherein the shank plate is spaced from the foot plate across a gap that reaches rearward from the seam; and
an attachment structure attaching the shank plate to the foot plate, wherein the attachment structure has a composite composition including a resin material containing reinforcing fibers, and the reinforcing fibers reach through the foot plate, across the gap, and through the shank plate.

19. A prosthetic foot structure as defined in claim 18, wherein the attachment structure crosses the gap at a location spaced rearward from the seam.

20. A prosthetic foot structure as defined in claim 18, wherein the attachment structure is located at least partially rearward of the seam.

21. A prosthetic foot structure as defined in claim 18, wherein the shank plate has a top surface, the foot plate has a bottom surface, and the reinforcing fibers are primarily aligned uni-directionally fully between the top surface and the bottom surface.

22. A prosthetic foot structure as defined in claim 21, wherein the attachment structure has a top portion in which the reinforcing fibers diverge above the top surface of the shank plate.

23. A prosthetic foot structure as defined in claim 22, further comprising a layer of fiber-reinforced resin material overlying the top surface of the shank plate and the top portion of the attachment structure.

24. A prosthetic foot structure as defined in claim 21, wherein the attachment structure has a bottom portion in which the reinforcing fibers diverge beneath the bottom surface of the foot plate.

25. A prosthetic foot structure as defined in claim 24, further comprising a layer of fiber-reinforced resin material underlying the bottom surface of the foot plate and the bottom portion of the attachment structure.

26. A prosthetic foot structure as defined in claim 18 wherein the foot plate has a composite composition including a resin material containing reinforcing fibers.

27. A prosthetic foot as defined in claim 26, wherein the reinforcing fibers in the foot plate are primarily aligned uni-directionally.

28. A prosthetic foot structure as defined in claim 26, wherein the foot plate has an elongated configuration with the toe portion at a forward end and the heel portion at a rearward end, and the reinforcing fibers in the foot plate are primarily aligned uni-directionally lengthwise of the foot plate.

29. A prosthetic foot structure as defined in claim 18, wherein the shank plate has a composite composition including a resin material containing reinforcing fibers.

30. A prosthetic foot as defined in claim 29, wherein the reinforcing fibers in the shank plate are primarily aligned uni-directionally.

31. A prosthetic foot structure as defined in claim 29, wherein the shank plate has an elongated configuration with the upper portion at a rearward end and the lower portion at a forward end, and the reinforcing fibers in the shank plate are primarily aligned uni-directionally lengthwise of the shank plate.

32. A prosthetic foot structure comprising:
- a foot plate having a composite composition including a resin material containing reinforcing fibers, wherein the foot plate has a toe portion and a heel portion;
- a shank plate having a composite composition including a resin material containing reinforcing fibers, wherein the shank plate has an upper portion that projects vertically upward, a lower portion that overlies the foot plate along a seam at which the shank plate is bonded to the foot plate, and the shank plate is spaced from the foot plate across a gap that reaches rearward from the seam; and
- an attachment structure attaching the shank plate to the foot plate, wherein the attachment structure has a composite composition including a resin material containing reinforcing fibers, and the reinforcing fibers in the attachment structure reach through the foot plate, across the gap, and through the shank plate.

33. A prosthetic foot structure as defined in claim 32, wherein the attachment structure crosses the gap at a location spaced rearward from the seam.

34. A prosthetic foot structure as defined in claim 32, wherein the attachment structure is located at least partially rearward of the seam.

35. A prosthetic foot structure as defined in claim 32, wherein the shank plate has a top surface, the foot plate has a bottom surface, and the reinforcing fibers in the attachment structure are aligned with one another fully between the top surface and the bottom surface.

36. A prosthetic foot structure as defined in claim 35, wherein the attachment structure has a top portion in which the reinforcing fibers diverge above the top surface of the shank plate.

37. A prosthetic foot structure as defined in claim 36, further comprising a layer of fiber-reinforced resin material overlying the top surface of the shank plate and the top portion of the attachment structure.

38. A prosthetic foot structure as defined in claim 35, wherein the attachment structure has a bottom portion in which the reinforcing fibers diverge beneath the bottom surface of the foot plate.

39. A prosthetic foot structure as defined in claim 38, further comprising a layer of fiber-reinforced resin material underlying the bottom surface of the foot plate and the bottom portion of the attachment structure.

* * * * *